United States Patent
Grady et al.

(10) Patent No.: US 9,386,933 B2
(45) Date of Patent: Jul. 12, 2016

(54) SYSTEMS AND METHODS FOR DETERMINATION OF BLOOD FLOW CHARACTERISTICS AND PATHOLOGIES THROUGH MODELING OF MYOCARDIAL BLOOD SUPPLY

(71) Applicant: HeartFlow, Inc., Redwood City, CA (US)

(72) Inventors: Leo J. Grady, Millbrae, CA (US); Charles A. Taylor, San Mateo, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

(21) Appl. No.: 14/529,495

(22) Filed: Oct. 31, 2014

(65) Prior Publication Data

US 2016/0058303 A1 Mar. 3, 2016

Related U.S. Application Data

(60) Provisional application No. 62/043,699, filed on Aug. 29, 2014.

(51) Int. Cl.
*G06F 19/00* (2011.01)
*G06F 19/10* (2011.01)
*G06F 19/26* (2011.01)
*A61B 5/026* (2006.01)
*A61B 5/00* (2006.01)

(52) U.S. Cl.
CPC ............. *A61B 5/026* (2013.01); *A61B 5/7275* (2013.01); *G06F 19/26* (2013.01); *G06F 19/3437* (2013.01)

(58) Field of Classification Search
None
See application file for complete search history.

(56) References Cited

U.S. PATENT DOCUMENTS

2012/0041324 A1* 2/2012 Taylor et al. ................. 600/508

OTHER PUBLICATIONS

Nagel et al. (Circulation (2003) vol. 108:432-437).*
Mouridsen et al. (NeuroImage (2006) vol. 33:570-579).*
Powell et al. (Application of Predictive Biosimulation to the Study of Atherosclerosis: development of the Cardiovascular Physiolab® Platform and Evaluation of CETP Inhibitor Therapy (2007) FOSBE) retrieved from the internet http://www.cmbi.ru.nl/edu/bioinf4/articles/pdf/sby_CV_Platform_Overview_Powell_etal_FOSBE_2007.pdf ).*
Bever et al. (abstract 13736: Mathematical Modeling Identifies Vessel Size and Geometry as Key Factors Determining the Rate of Plaque Development in Mouse and Human; Circulation (2012) 126:A13736' pp. 1-2).*

* cited by examiner

*Primary Examiner* — Lori A Clow
(74) *Attorney, Agent, or Firm* — Bookoff McAndrews, PLLC (57) ABSTRACT

Systems and methods are disclosed for evaluating a patient with vascular disease. One method includes receiving one or more vascular models associated with either the patient or with a plurality of individuals; receiving observed perfusion information associated with the patient; and estimating, using one or more computer processors, one or more blood flow characteristics or one or more pathological characteristics of the patient based on the observed perfusion information and the one or more vascular models.

20 Claims, 6 Drawing Sheets

SYSTEMS AND METHODS FOR DETERMINATION OF BLOOD FLOW CHARACTERISTICS AND PATHOLOGIES THROUGH MODELING OF MYOCARDIAL BLOOD SUPPLY

RELATED APPLICATION(S)

This application claims priority to U.S. Provisional Application No. 62/043,699 filed Aug. 29, 2014, the entire disclosure of which is hereby incorporated herein by reference in its entirety.

FIELD OF THE DISCLOSURE

Various embodiments of the present disclosure relate generally to disease assessment, treatment planning, and related methods. More specifically, particular embodiments of the present disclosure relate to systems and methods for determining blood flow characteristics and pathologies through modeling of myocardial blood supply.

BACKGROUND

Coronary artery disease is a common ailment that affects millions of people. Coronary artery disease may cause the blood vessels providing blood to the heart to develop lesions, such as a stenosis (abnormal narrowing of a blood vessel). As a result, blood flow to the heart may be restricted. A patient suffering from coronary artery disease may experience chest pain, referred to as chronic stable angina during physical exertion or unstable angina when the patient is at rest. A more severe manifestation of disease may lead to myocardial infarction, or heart attack. Significant strides have been made in the treatment of coronary artery disease including both medical therapy (e.g. statins) or surgical alternatives (e.g., percutaneous coronary intervention (PCI) and coronary artery bypass graft surgery (CABG)). Invasive assessments are commonly used to assess the type of treatment a patient may receive. However, indirect or noninvasive assessments for formulating a patient treatment are being explored and developed.

One way of assessing the need for treatment, is observing blood supply to tissue, since cardiovascular disease reduces blood supply to tissue (e.g., myocardial tissue). Several diagnostic modalities (e.g., computed tomography (CT angiography) and magnetic resonance imaging (MR angiography)) provide an assessment of blood supply to tissue (e.g., perfusion, viability, or biomedical aspects of the tissue). While blood supply may provide some input for evaluating medical treatment, assessment of blood supply alone is inadequate for determining a targeted treatment. Heart disease is contingent on several more factors.

The inadequacy is made apparent by the fact that medical treatments prescribed are often more extreme than necessary. For example, PCI and bypass grafts are highly overused. In addition, PCI and bypass grafts are sometimes not used effectively, for instance, due to incorrect placement or placement at stenoses that are not functionally significant. Thus, at a threshold level, a need exists to accurately assess the severity of cardiovascular disease in determining which treatment to apply to a patient. Furthermore, for PCI and bypass grafts, an accurate assessment of locations for applying treatment is important. Thus, a desire exists for improving treatment by targeting treatment sites, both by accurately determining the severity of a disease and by pinpointing locations effective in treating the disease.

The foregoing general description and the following detailed description are exemplary and explanatory only and are not restrictive of the disclosure.

SUMMARY

According to certain aspects of the present disclosure, systems and methods are disclosed for determining blood flow characteristics and pathologies through modeling of myocardial blood supply.

One method includes: receiving one or more vascular models associated with either the patient or with a plurality of individuals; receiving observed perfusion information associated with the patient; and estimating, using one or more computer processors, one or more blood flow characteristics or one or more pathological characteristics of the patient based on the observed perfusion information and the one or more vascular models.

In accordance with another embodiment, a system for evaluating a patient with vascular disease comprises: a data storage device storing instructions for evaluating a patient with vascular disease; and a processor configured for: receiving one or more vascular models associated with either the patient or with a plurality of individuals; receiving observed perfusion information associated with the patient; and estimating, using one or more computer processors, one or more blood flow characteristics or one or more pathological characteristics of the patient based on the observed perfusion information and the one or more vascular models.

In accordance with another embodiment, a non-transitory computer readable medium for use on a computer system containing computer-executable programming instructions for performing a method of evaluating a patient with vascular disease, the method comprising: receiving one or more vascular models associated with either the patient or with a plurality of individuals; receiving observed perfusion information associated with the patient; and estimating, using one or more computer processors, one or more blood flow characteristics or one or more pathological characteristics of the patient based on the observed perfusion information and the one or more vascular models.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

Coronary artery disease is a common ailment, by which blood flow to the heart may be restricted. While significant strides have been made in the treatment of coronary artery disease, the treatment is often misplaced or excessive. For example, patients often undergo invasive surgical treatments when medication may suffice. Patients are sometimes subjected to treatments that may not change their condition. In some situations, patients even undergo treatments that ultimately worsen their condition. Thus, a need exists to accurately assess the severity of cardiovascular disease in selecting a course of treatment. Additionally, a more accurate assessment of locations for applying treatments may provide more targeted treatment.

One way of assessing the need for treatment is by observing blood supply to the patient's tissue, since cardiovascular disease typically involves a reduction in blood supply to tissue (e.g., myocardial tissue). Several diagnostic modalities (e.g., computed tomography (CT angiography) and magnetic resonance imaging (MR angiography)) provide an assessment of blood supply to tissue (e.g., perfusion, viability, or biomedical aspects of the tissue). However, assessment of blood supply, alone, is inadequate for determining appropriate treatment. For example, blood supply analysis, itself, cannot accurately localize a source of cardiovascular disease and indicate a severity of a disease. Meanwhile, recent advances in imaging and computational modeling have provided a means to virtually simulate blood flow for a patient, based on the creation of a cardiovascular model for the patient.

The present disclosure includes systems and methods for improving disease and treatment assessment using metrics available from virtual simulations, thus leveraging advances in biomechanical computational modeling with observational data about patient blood supply in order to localize and determine the severity of cardiovascular disease. In one embodiment, the present disclosure includes working backward (e.g., in a so-called "inverse" fashion) from the observational blood supply data to infer a likely computational model that describes the patient's cardiovascular disease. In other words, the disclosure includes finding a computational model that may explain the patient's observed blood supply data. In one embodiment, inferring the computational model may include creating a cardiovascular model for the patient. The determined computational model (and/or cardiovascular model) may provide information regarding severity and localization of cardiovascular disease, that may form the basis for a patient treatment.

For example, the present disclosure may initially include determining a relationship between blood flow characteristics and/or pathological characteristics. The disclosure may further include determining how those blood flow characteristics and/or pathological characteristics relate to blood supply to tissue. For example, a blood flow characteristic and/or a pathological characteristic including venous obstruction or low-flow may relate to low blood supply to tissue. The present disclosure may further include observing variables associated with a patient's tissue, for instance, blood supply to the patient's tissue. Patient blood flow and patient pathological characteristics may be estimated, given the known relationships between blood flow characteristics, pathological characteristics, and tissue blood supply and the observed patient blood supply to tissue.

In some embodiments, patient blood flow and/or patient pathological characteristics may be computed from a cardiovascular model for the patient. For example, one embodiment may include constructing a cardiovascular model for the patient, using the observed blood supply to the patient's tissue and the determined relationship between blood flow characteristics, pathological characteristics, and blood supply. Virtual simulations of blood flow through the cardiovascular model, for instance, may be used to compute the inferred patient blood flow and/or patient pathological characteristics. The constructed patient cardiovascular model, estimated patient blood flow, and/or estimated patient pathological characteristics may reflect a patient condition contributing to the observed blood supply to patient tissue. The patient condition may include characterizations of disease localization and severity. Knowing disease severity and localizing the disease permits formulation of appropriate, effective treatment. For the present disclosure, "patient" may refer to any individual of interest.

Figure 1:
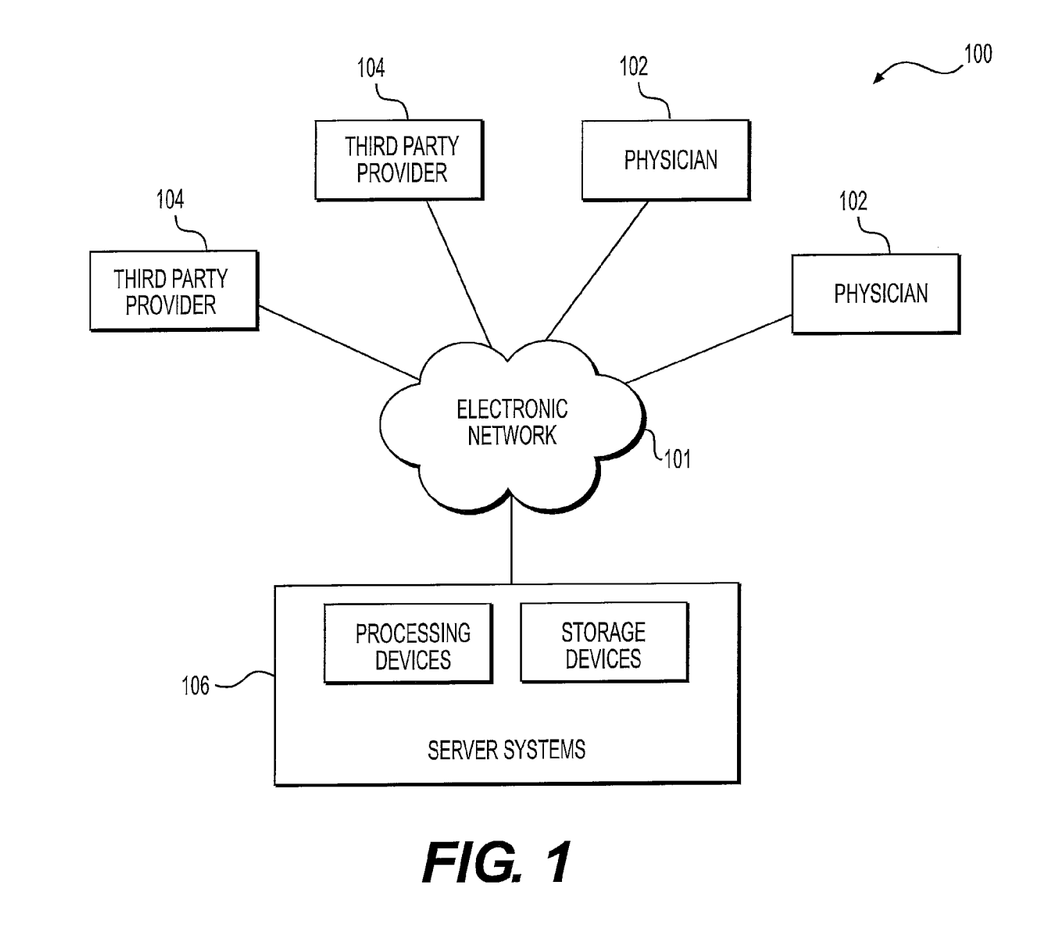
FIG. 1 is a block diagram of an exemplary system and network for determining blood flow characteristics and pathologies through modeling of myocardial blood supply, according to an exemplary embodiment of the present disclosure.

Referring now to the figures, FIG. 1 depicts a block diagram of an exemplary system 100 and network for determining blood flow characteristics and pathologies through modeling of myocardial blood supply, according to an exemplary embodiment. Specifically, FIG. 1 depicts a plurality of physicians 102 and third party providers 104, any of whom may be connected to an electronic network 101, such as the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific information, such as age, medical history, blood pressure, blood viscosity, patient activity or exercise level, etc. Physicians 102 and/or third party providers 104 may transmit the anatomical images and/or patient-specific information to server systems 106 over the electronic network 101. Server systems 106 may include storage devices for storing images and data received from physicians 102 and/or third party providers 104. Server systems 106 may also include processing devices for processing images and data stored in the storage devices.

Figure 2A:
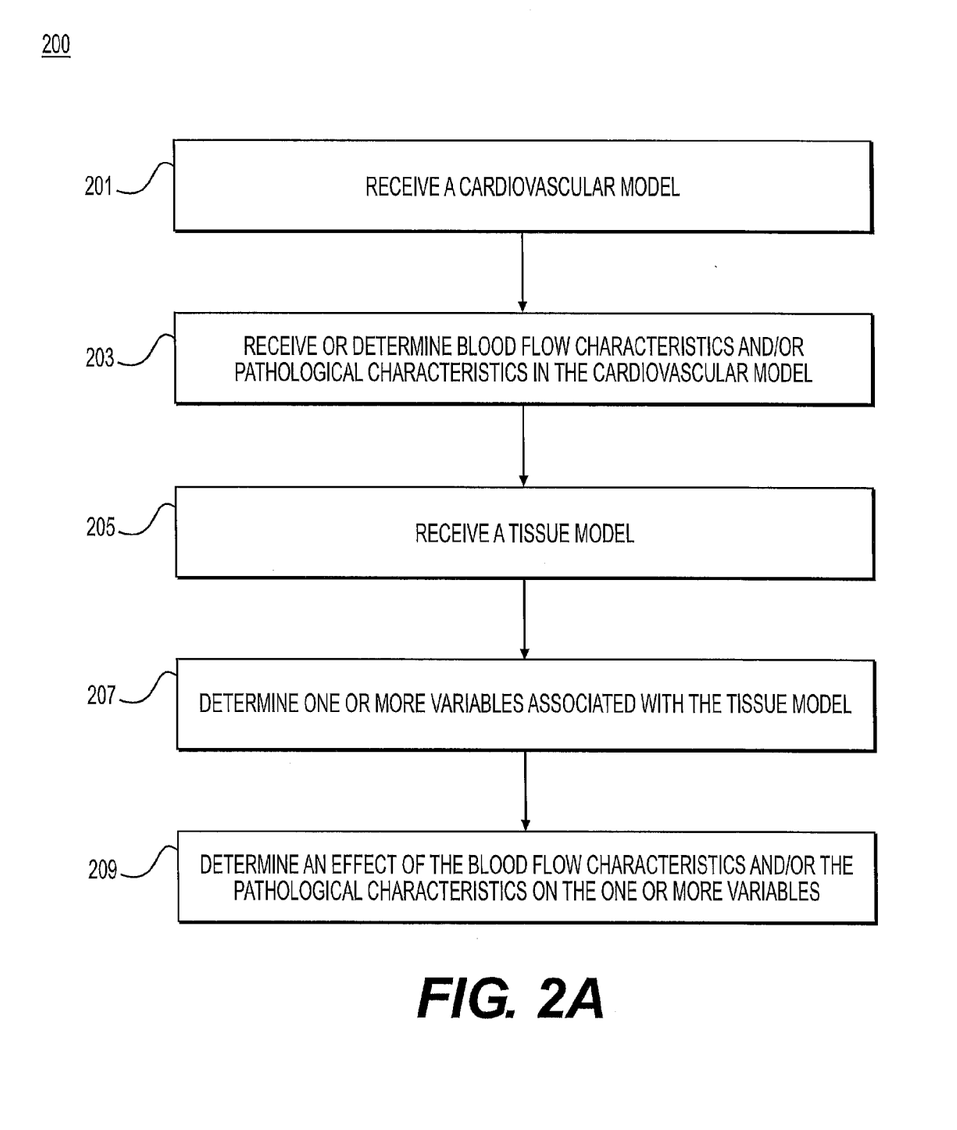
FIG. 2A is a block diagram of an exemplary method of determining the relationship between blood flow characteristics, pathologies, and tissue model variables, according to an exemplary embodiment of the present disclosure.
Figure 2B:
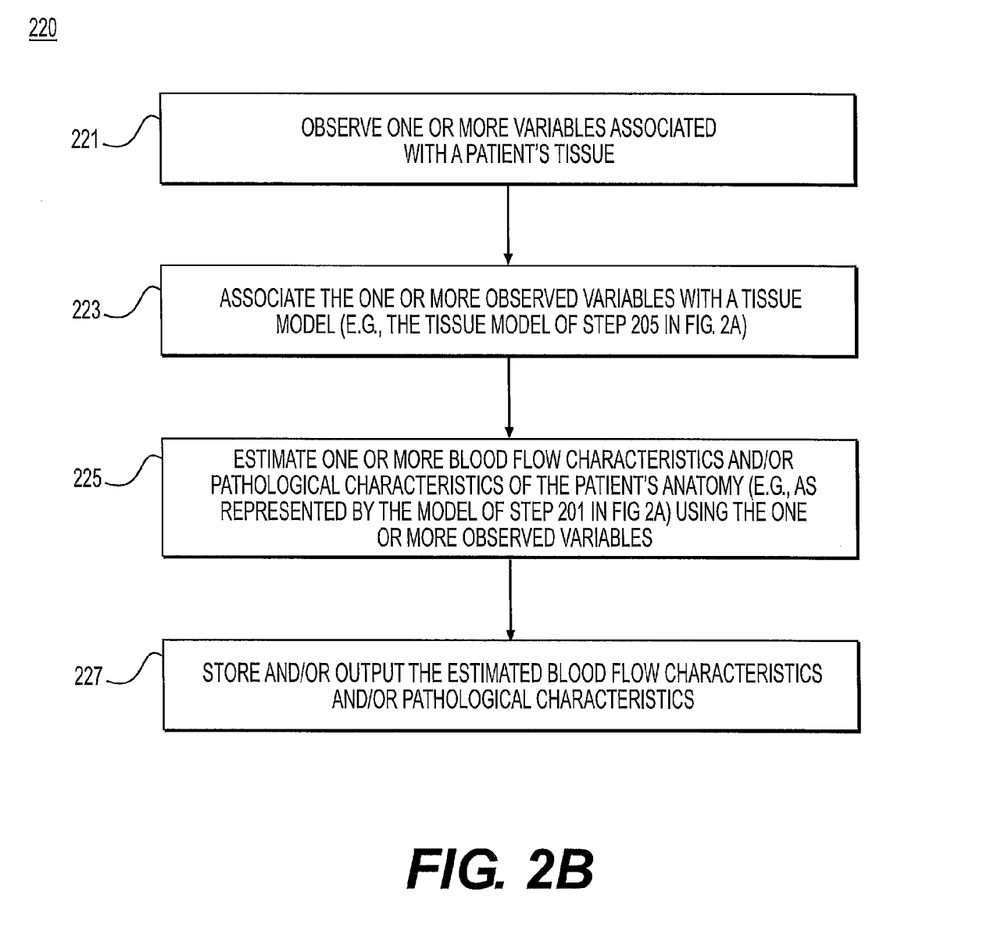
FIG. 2B is a block diagram of an exemplary method of estimating blood flow characteristics and/or pathologies using a set of observed tissue variables, according to an exemplary embodiment of the present disclosure.

FIGS. 2A and 2B, in combination, provide steps for determining blood flow characteristics and pathologies through modeling of myocardial or observed blood supply, according to an exemplary embodiment. In one embodiment, FIG. 2A may include steps to determine how characteristics derived from a cardiovascular model may affect variables measured from a tissue model. For example, the steps in FIG. 2A may include determining the relationship between a cardiovascular model's blood flow and/or pathological characteristics and a tissue model's associated perfusion values or myocardial wall motion values. In one embodiment, FIG. 2B may include receiving or determining observed variable values measured from patient tissue (e.g., blood supplied to the patient tissue) and estimating variables (e.g., vessel characteristics, including blood flow characteristics and/or pathological characteristics) using the relationship found from FIG. 2A. In other words, the method of FIG. 2A includes determining expected perfusion, given one or more anatomies and tissue models. FIG. 2B includes acquiring perfusion data, and then performing forward modeling with relationships found in FIG. 2A in order to determine anatomy and tissue models (including blood flow characteristics and/or pathological characteristics) that may give rise to the acquired perfusion data. For instance, an anatomical model, alone, may not provide insight into an extent or impact of luminal narrowing within various parts of the anatomical model. Forward modeling may provide an expected perfusion map, which may be compared against, for instance, an acquired or observed patient perfusion map.

In a further embodiment, a user may input variations into assessments performed in the method of FIG. 2A. The variations may provide insight into agreement between actual and modeled perfusion data for the method of FIG. 2B. For example, a user may select or input one or more types of disease (e.g., plaque severities) and/or one or more locations of potential plaque within an anatomical model. For the method of FIG. 2A, a user selection or input may prompt a showing of how the characteristics input by the user may influence perfusion. For the method of FIG. 2B, a user selection or input may prompt a showing of agreement between modeled perfusion data and observed (e.g., patient-specific) perfusion data, given the user selection or input. In other words, some embodiments of the methods of FIG. 2A and/or FIG. 2B may include providing users with options to test various anatomical, flow, and/or boundary conditions to see how these conditions may impact simulated perfusion (e.g., in the form of simulated luminal narrowing).

For instance, the methods of FIG. 2A and/or 2B may include rendering one or more user interfaces for receiving such user input, where the user interface may also include a rendering of how the user's input may improve or decrease agreement between actual and modeled perfusion data. In an exemplary case, the renderings may include pictorial elements (e.g., representations of anatomy, perfusion or blood flow, plaque and plaque severities, etc.). In another exemplary case, the renderings may include graphs, plots, or collections of data. The renderings may further include color-coding, annotations, gradient shading, etc. An understanding of factors that improve perfusion may provide the basis for targeted treatment planning. In one embodiment, an extension of the methods of FIGS. 2A and 2B may include treatment analysis. For example, system 100 may further determine and/or output a treatment for a patient, based on the patient blood flow characteristics or patient pathological characteristics found through forward modeling using the methods of FIGS. 2A and 2B. The treatment may be determined automatically, for example, based on analyses to optimize perfusion in light of the patient blood flow characteristics or patient pathological characteristics. Alternately or in addition, the output treatment may be based on the user selections or inputs, for instance, simulating various treatments and/or treatment locations and observing how the simulations improve perfusion.

Figure 3A:
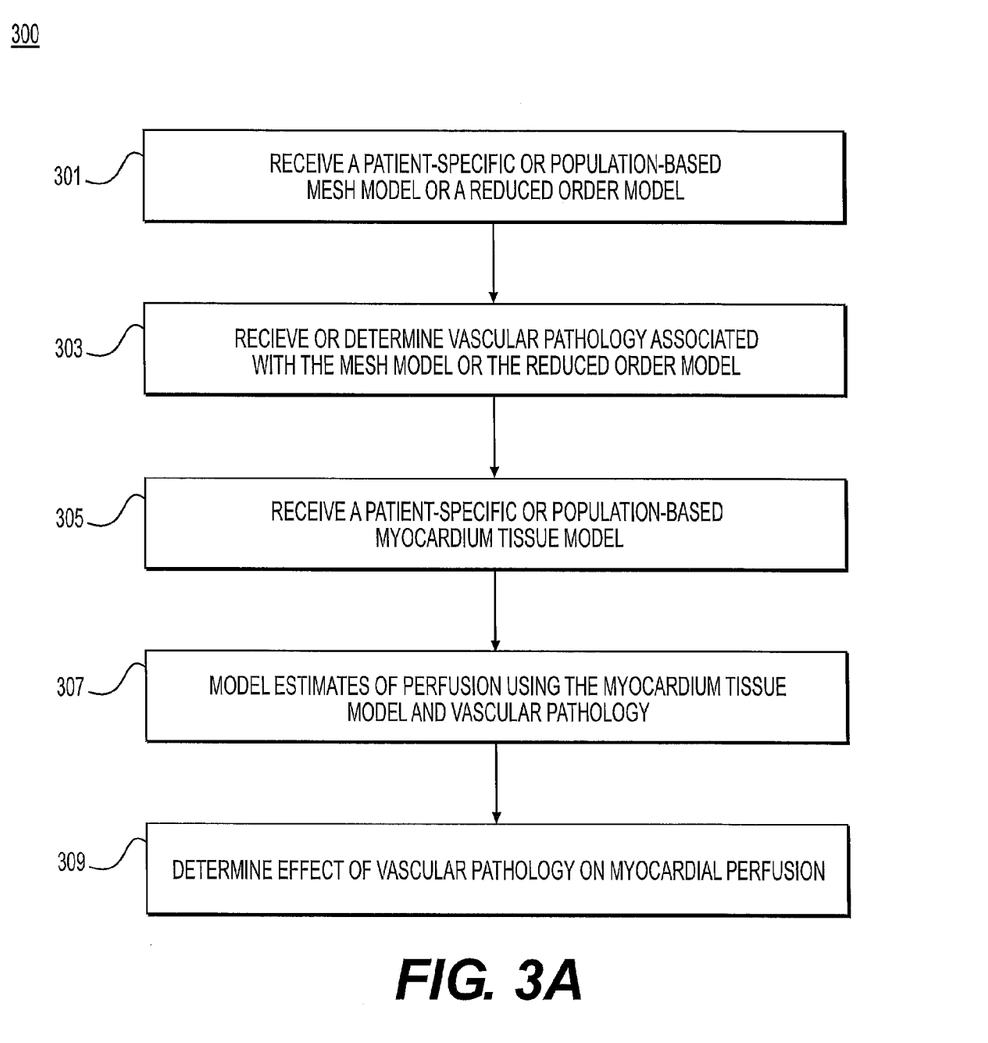
FIG. 3A is a block diagram of an exemplary method of determining the relationship between blood flow characteristics, pathologies, and tissue variables associated with one or more of perfusion deficit and myocardial wall motion, according to an exemplary embodiment of the present disclosure.
Figure 3B:
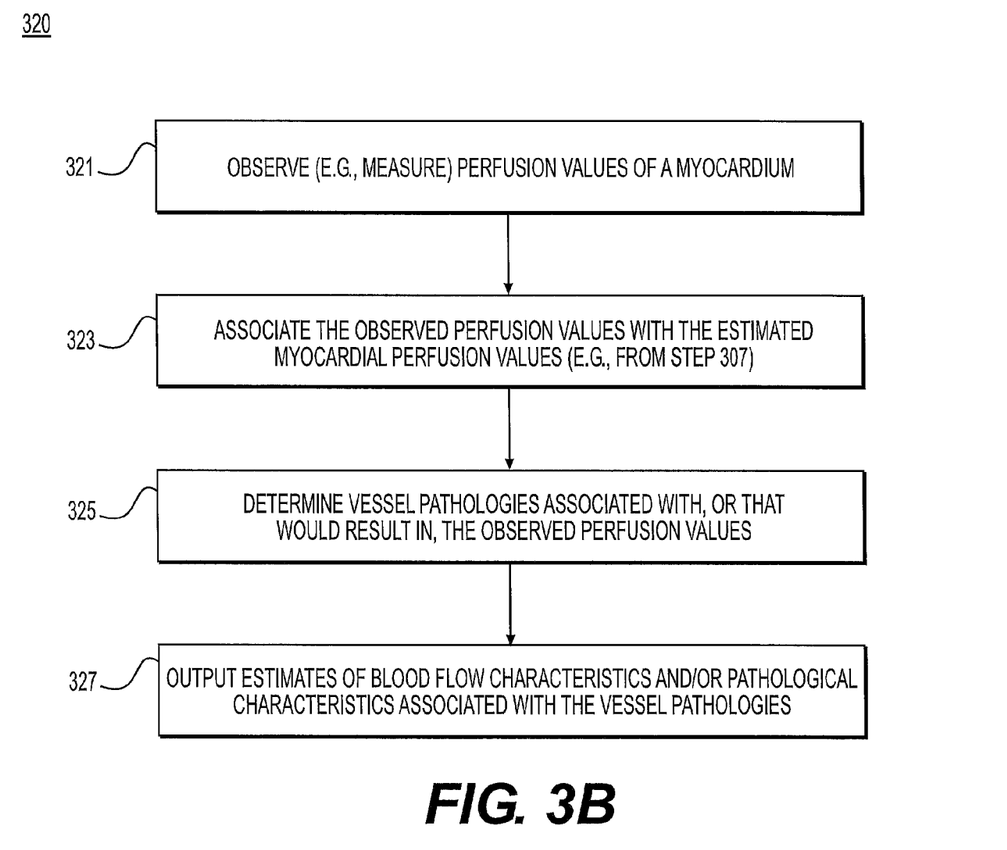
FIG. 3B is a block diagram of an exemplary method of estimating blood flow characteristics and pathologies using observed perfusion values, according to an exemplary embodiment of the present disclosure.
Figure 3C:
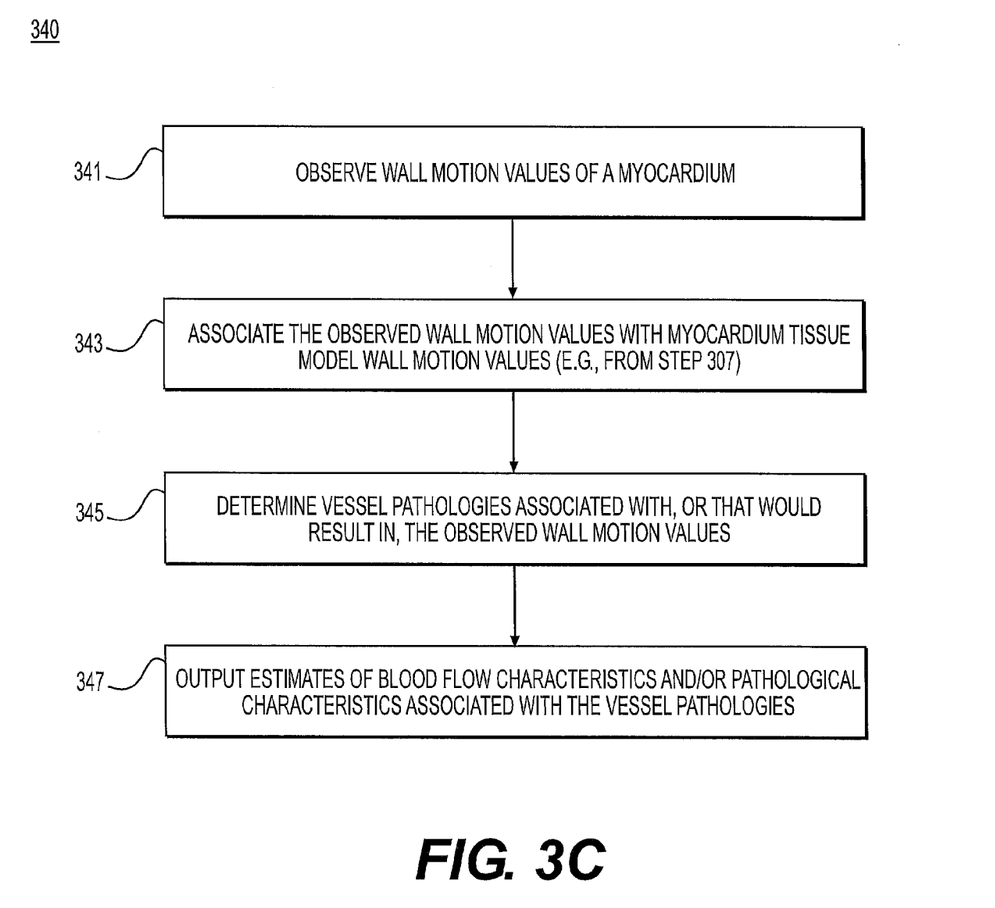
FIG. 3C is a block diagram of an exemplary method of estimating blood flow characteristics and pathologies using observed wall motion values, according to an exemplary embodiment of the present disclosure.

FIGS. 3A-3C may provide specific embodiments for the methods of FIGS. 2A and 2B. For example, FIG. 3A may include an embodiment of the process for finding a relationship between blood flow or pathological characteristics and tissue model characteristics. FIGS. 3B and 3C may provide specific embodiments pertaining to perfusion deficit and myocardial wall motion, respectively. For example, FIG. 3B may include a method using the relationship found in FIG. 3A to determine vessel pathologies that may explain perfusion values observed from a patient's myocardium. Similarly, FIG. 3C may include a method using the relationship found in FIG. 3A to determine vessel pathologies that may explain wall motion values observed from a patient's myocardium.

FIG. 2A is a block diagram of an exemplary method 200 of determining the relationship between blood flow characteristics, pathologies, and tissue model variables, according to an exemplary embodiment. The method of FIG. 2A may be performed by server systems 106, based on information, images, and data received from physicians 102 and/or third party providers 104 over electronic network 101.

In one embodiment, step 201 includes receiving a cardiovascular model (e.g., in an electronic storage medium over electronic network 101). In one embodiment, the cardiovascular model may include a cardiovascular model of an individual (e.g., a patient or individual of interest). For example, the cardiovascular model may be derived from images of the individual, acquired via imaging or scanning modalities (e.g., CT scans or MR imaging). In one embodiment, step 203 may include receiving or determining blood flow characteristics and/or pathological characteristics in the cardiovascular model. Step 205 may include receiving a tissue model (e.g., in an electronic storage medium). Step 207 may include determining one or more variables associated with the tissue model (e.g., perfusion values or myocardial wall motion values). For example, step 207 may include defining or identifying one or more variables that may be measured from the tissue model. For instance, the one or more variables may include variables that (directly or indirectly) measure blood supply to the tissue. Step 207 may further include calculating the values of the one or more defined or identified variables.

In one embodiment, step 209 may include determining a relationship between the one or more variables associated with the tissue model and the blood flow characteristics and/or pathological characteristics in the cardiovascular model. For example, step 209 may include determining a relationship between blood flow characteristics and pathological characteristics. In addition, step 209 may include determining an effect of blood flow characteristics and/or pathological characteristics on the one or more variables of the tissue model. In other words, step 209 may include determining resultant tissue model variables, given a set of blood flow and pathological conditions.

FIG. 2B is a block diagram of an exemplary schematic of a method 220 of estimating blood flow characteristics and pathologies using a set of observed tissue variables, according to an exemplary embodiment. The method of FIG. 2B may be performed by server systems 106, based on information, images, and data received from physicians 102 and/or third party providers 104 over electronic network 101.

In one embodiment, method 220 may include step 221 of actually measuring and/or observing one or more variables of a patient's tissue. For example, step 221 may include defining or identifying one or more variables to observe in patient tissue (e.g., perfusion values or myocardial wall motion values), and then monitoring measurements of the one or more variables via, e.g., imaging, in vitro diagnostics, visual inspection of the patient, etc. Step 223 may include associating the one or more observed variables with a tissue model (e.g., the tissue model of step 205). Step 223 may further include storing the one or more observed variables electronically (e.g., via an electronic storage medium, RAM, etc.). In one embodiment, step 225 may include estimating one or more blood flow characteristics and/or pathological characteristics of the patient's anatomy. For example, the estimating performed in step 225 may indicate that the patient's anatomy may be represented by the cardiovascular model from step 201. In other words, step 225 may include estimating the patient blood flow and patient pathological characteristics in view of the one or more observed variables associated with the patient. In some cases, step 225 may be performed using a computing processor. In one embodiment, step 227 may include outputting the estimates of the one or more patient blood flow characteristics and/or patient pathological characteristics (e.g., to an electronic storage medium).

In some cases, a further step may include determining or recommending a treatment based on the estimates of the one or more patient blood flow characteristics and/or patient pathological characteristics. For example, determining or recommending a treatment may include receiving or creating one or more treatments associated with one or more blood flow conditions or pathological conditions. Determining or recommending a treatment may additionally or alternatively include identifying treatments associated with one or more combinations of blood flow characteristics and/or pathological characteristics. Method 220 may further include finding or recommending treatment options that may be appropriate, given the estimated patient blood flow characteristics and/or patient pathological characteristics.

FIG. 3A is a block diagram of an exemplary method 300 of determining the relationship between blood flow characteristics, pathologies, and tissue variables associated with one or more of perfusion deficit and myocardial wall motion, according to an exemplary embodiment. The method of FIG. 3A may be performed by server systems 106, based on information, images, and data received from physicians 102 and/or third party providers 104 over electronic network 101.

Perfusion deficit analysis and myocardial wall motion analysis may be useful for assessing the lack of blood supply to the myocardium of the heart. Perfusion deficit may be assessed with single photon emission computed tomography (SPECT), positron emission tomography (PET), magnetic resonance (MR) perfusion, or coronary tomography (CT) perfusion imaging. Myocardial wall motion analysis may be assessed with ultrasound or other forms of dynamic imaging (e.g., MR cine images, tagged MR, or full phase CT imaging). Areas of the myocardium that do not receive adequate blood supply may exhibit abnormal motion. Thus, observing myocardial wall motion may be one way to evaluate perfusion.

However, perfusion deficit studies may not provide an assessment of the source of the perfusion deficit. For example, a physician trying to determine an effective patient treatment may not receive clear guidance from a perfusion deficit study alone. Similarly, wall motion studies (e.g., associated with myocardial wall motion) may not provide an assessment of the source of the wall motion abnormality and therefore also may not provide clear guidance on a targeted treatment option. Consequently, perfusion deficit information and/or wall motion information may be used to determine that a blood flow problem exists, but perfusion deficit information and/or wall motion information, alone, may be insufficient in determining effective treatment.

Method 300 of FIG. 3A may assess the source of the perfusion deficit (e.g., in conjunction with method 320 of FIG. 3B) and/or the source of the wall motion abnormality (e.g., with method 340 of FIG. 3C). Knowledge of the source of the perfusion deficit and/or the wall motion abnormality may help determine an appropriate treatment for a given patient.

In one embodiment, step 301 may include receiving a coronary artery model (e.g., in an electronic storage medium). For example, the coronary artery model may include a three-dimensional (3D) mesh model or a one-dimensional (1D) reduced order model. In some cases, the coronary artery model may include a patient-specific model (e.g., a model obtained via segmentation of a patient cardiac CT image). Alternately or in addition, the coronary artery model may include a generalized model based on population averages. Step 301 may include discerning coronary geometry from imaging and further include discretizing the coronary tree based on potential locations of plaque and/or severity of potential plaque. In one embodiment, step 303 may include receiving or identifying vascular pathology or pathological state associated with the coronary artery model.

In one embodiment, step 305 may include receiving a myocardium tissue model (e.g., in an electronic storage medium). For example, the patient-specific myocardium tissue model may include a 3D volumetric mesh model or a two-dimensional (2D) surface mesh model. In some cases, the myocardium tissue model may include a patient-specific model (e.g., obtained via segmentation of a patient cardiac CT image). Alternately or in addition, the myocardium tissue model may include a generalized model based on population averages. Certain blood flow characteristics and/or perfusion characteristics may be associated with the myocardium tissue model.

In one embodiment, step 307 may include selecting or evaluating a relationship between the coronary artery model and the myocardium tissue model. For example, step 307 may include finding the connection between vascular pathology and tissue, in terms of computational fluid dynamics. For instance, step 307 may include modeling perfusion using known methods (e.g., solving a reduced order model of blood flow in a network of blood vessels generated to fill the tissue model, diffusion modeling, nearest-neighbor modeling).

In one embodiment, modeling perfusion in step 307 may include performing constrained constructive optimization. One instance of constrained constructive optimization may include establishing one or more perfusion territories, for example, within the coronary artery model, using the myocardium tissue model. The modeling of step 307 may further include parameterizing one or more locations of plaque within the one or more perfusion territories. Such parameterizing of location(s) of plaque may be performed on either generic or patient-specific coronary artery models or myocardium tissue models. Provided with parameterized location(s) of plaque, forward modeling may be used to model the quantity and rate of blood flow that may pass through the one or more established perfusion territories. Modeling perfusion may relate the vascular pathologies to perfusion through the tissue model. In other words, step 307 may include recognizing correspondence between certain vascular pathologies and perfusion values found from the modeling.

In one embodiment, step 309 may include assessing the effect of vascular pathology on myocardial perfusion. For example, step 309 may include analyzing results of the modeling of step 307 to determine how fluid dynamics change with respect to vascular pathology. By extension, the changes in fluid dynamics associated with vascular pathology may impact myocardial perfusion. Step 309 may involve determining the influence that vascular pathology may have on myocardial perfusion.

In one embodiment, step 309 may include analyzing effects of various severities of potential plaque within a coronary tree discretized into multiple locations. In such an instance, step 309 may include receiving or prompting user input for severities of the potential plaque and/or locations of possible plaque within the discretized coronary tree. Alternately, the selection of potential plaque severity and location may be automated. In one instance, step 309 may include modeling perfusion throughout one or more perfusion territories that encompass the selected possible locations and luminal narrowing associated with the possible plaque severity. Alternately, the perfusion may be modeled through selected portions of the one or more perfusion territories, where the selected portions of the one or more perfusion territories may include one or more of the selected possible locations and luminal narrowing associated with the possible plaque severity. The selected portions of the one or more perfusion territories may be selected automatically or by one or more users (e.g., upon prompting of user input).

FIG. 3B is a block diagram of an exemplary method 320 of estimating blood flow characteristics and pathologies using observed perfusion values, according to an exemplary embodiment. The method of FIG. 3B may be performed by server systems 106, based on information, images, and data received from physicians 102 and/or third party providers 104 over electronic network 101.

In one embodiment, step 321 may include observing perfusion values for a patient's myocardium (e.g., for the patient associated with the artery model and tissue model of steps 301 and 303). The perfusion values may include measured or observed values for one or more perfusion variables. In one embodiment, perfusion values may be observed via SPECT, PET, MR perfusion, or CT perfusion imaging.

In one embodiment, step 323 may include associating the observed perfusion values with the myocardial perfusion values in the myocardium tissue model (e.g., from step 303). For example, step 323 may include making the associations by registering the myocardium tissue model to image(s) from which the perfusion values were observed (e.g., using a computational processor). Step 323 may further include storing the observed perfusion values electronically (e.g., via an electronic storage medium, RAM, etc.).

In one embodiment, step 325 may include using a computing processor to determine the set of vessel pathologies that may cause the observed perfusion values. For example, step 325 may include systematically deforming the coronary model to represent pathologies at one or more different locations (e.g., by applying stenoses of different severities at given locations in the coronary model). For each of the deformations, step 325 may include applying computational fluid dynamics and determining a set of resulting myocardial perfusion values.

Furthermore, step 325 may include identifying one or more locations in the coronary model, creating one or more hypothetical severities of stenoses, and then applying these hypothetical stenos(es) at the location(s). Some or all of the hypothetical severities of stenoses may be applied at each of the location(s) identified. In such cases, part of step 325 may include determining which of the one or more hypothetical severities of stenoses should be applied at which of the one or more locations.

One form of step 325 may also include creating or selecting an estimate of the coronary model (e.g., a model of stenosis and computed blood flow). For example, the created or selected coronary model may include a coronary model that agrees with the observed data (e.g., by selecting the coronary model that results in a minimum of the maximum perfusion difference between the observed and computed myocardium models). For instance, step 325 may include comparing various coronary models and identifying or selecting a model that would most likely produce the observed data. From the estimated coronary model, various blood flow characteristics including, fractional flow reserve, coronary flow reserve, etc., may be computed, including, fractional flow reserve, coronary flow reserve, etc. Another form of step 325 may include using machine learning methods to learn a set of vessel pathologies that may correspond to the observed variables.

In one embodiment, step 327 may include outputting the estimates of the one or more blood flow characteristics and/or pathological characteristics associated with the patient vessel pathologies (e.g., based on the assessment of step 309). For example, step 327 may include outputting an estimate of one or more stenosis locations, stenosis severities, and/or one or more fractional flow reserves to an electronic storage medium. In one embodiment, the estimates of the one or more blood flow characteristics and/or pathological characteristics may be output to an electronic storage medium. Step 327 may further include determining which of the estimates to output.

FIG. 3C is a block diagram of an exemplary method 340 of estimating blood flow characteristics and pathologies using observed wall motion values, according to an exemplary embodiment. The method of FIG. 3C may be performed by server systems 106, based on information, images, and data received from physicians 102 and/or third party providers 104 over electronic network 101.

In one embodiment, step 341 may include observing wall motion values for the patient's myocardium (e.g., for the patient associated with the artery model and tissue model of steps 301 and 303). The wall motion values may include measured or observed values for one or more wall motion variables. In one embodiment, wall motion values may be observed via ultrasound, MR, or CT imaging.

In one embodiment, step 343 may include associating the observed wall motion values with the wall motion values in the myocardium tissue model (e.g., from step 303). For example, step 343 may include making the associations by registering the myocardium tissue model to image(s) from which the perfusion values were observed using a computational processor at multiple frames. Wall motion values may be determined by computing displacement of the myocardial wall between frames. Step 343 may further include storing the wall motion variables electronically (e.g., via an electronic storage medium, RAM, etc.).

In one embodiment, step 345 may include using a computing processor to determine the set of vessel pathologies that would result in the observed wall motion values. For example, step 345 may include systematically deforming the coronary model to represent pathologies at different locations (e.g., by applying stenoses of different severities at equally spaced locations in the coronary model). For each of the deformations, step 345 may include applying computational fluid dynamics and determining a set of resulting myocardial perfusion values. Step 345 may further include mapping these perfusion values to wall motion values.

In addition, step 345 may include identifying one or more locations in the coronary model, creating one or more hypothetical severities of stenoses, then applying these hypothetical severities of stenos(es) at the location(s). Some or all of the hypothetical severities of stenoses may be applied at each of the location(s) identified. In such cases, part of step 345 may include determining which of the one or more locations to apply to which of the one or more hypothetical severities of stenoses.

One form of step 345 may include creating or selecting an estimate of the coronary model (stenosis and computed blood flow) as the coronary model (stenosis and computed blood flow). For example, the created or selected coronary model may include a model that reflects the observed data (e.g., by selecting the coronary model that results in a minimum of the maximum wall motion difference between the observed and computed myocardium models). For instance, step 345 may include comparing various coronary models and selecting a model from the comparison that would most likely produce the observed data. The estimated coronary model may be used to compute blood flow characteristics, including fractional flow reserve, coronary flow reserve, etc. Another form of step 345 may include using machine learning methods to learn a set of vessel pathologies that may correspond to the observed variables.

In one embodiment, step 347 may include outputting the estimates of the one or more blood flow characteristics and/or pathological characteristics associated with the vessel pathologies (e.g., based on the assessment of step 309). For example, step 347 may include outputting an estimate of one or more stenosis locations, stenosis severities, and one or more fractional flow reserve values to an electronic storage medium. In one embodiment, the estimates of the one or more blood flow characteristics and/or pathological characteristics may be output to an electronic storage medium. Step 347 may further include determining which of the estimates to output.

The present disclosure may further apply to organs and tissues other than the heart. For example, the present disclosure may apply to any scenarios where it is desirable to relate a measurement of the function of the tissue or organ to a consideration of the blood supply through the arterial network supplying that tissue or organ. One such scenario may involve relating perfusion measured during a functional brain imaging study to the vessels supplying the brain, in order to identify the location of disease affecting cerebral blood supply. This understanding of cerebral blood supply may be important for patients that have had a stroke or a transient ischemia attack (TIA).

Alternatively or additionally, the present disclosure may be useful in relating disease in vessels supplying a patient's legs, to regions of reduced flow in the muscles of the lower extremities. In one embodiment, the reduced flow may be observed (e.g., imaged) during or after physical activity. For example, perfusion imaging may be performed using magnetic resonance imaging methods while the patient is exercising on an MR-compatible ergometer. Severity or location of disease in vessels may be determined from observed exercise perfusion values. Treatments may then be formulated based on this understanding of the disease.

In an alternative embodiment, the present disclosure may be used to quantify the significance of renal artery disease. For example, the embodiment may include identifying relationships between a vascular model (e.g., generated using magnetic resonance angiography data) and a tissue model (e.g., generated using kidney oxygenation measurements obtained with BOLD (Blood Oxygen-Level-Dependent) magnetic resonance imaging). Given an individual's kidney oxygenation measurements, a patient vascular model may be built using the known relationships. The significance of the patient's renal artery disease may be found from the patient vascular model.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of evaluating a patient with vascular disease, the method comprising:
    receiving a tissue model of the patient;
    receiving a vascular model defining one or more vessel pathologies at a location of vasculature supplying blood to the tissue model;
    modeling perfusion resulting from a first vessel pathology of the vascular model supplying blood to at least a portion of the tissue model;
    computing, from the modeled perfusion resulting from the first vessel pathology, a first tissue characteristic value of the tissue model in response to the first vessel pathology, the tissue characteristic including a measure of tissue viability, a tissue capacity to change blood flow, a tissue irregularity, a tissue electrical property, and/or a tissue mechanical property;
    modeling perfusion resulting from a second vessel pathology of the vascular model supplying blood to at least a portion of the tissue model;
    computing, from the modeled perfusion resulting from the second vessel pathology, a second tissue characteristic value of the tissue model in response to the second vessel pathology;
    determining an effect of vessel pathology on the at least one tissue characteristic, from a comparison of the first tissue characteristic to the second tissue characteristic;
    receiving an observed tissue characteristic value associated with a patient; and
    estimating, using one or more computer processors, one or more patient pathological characteristics at a location in the patient's anatomy using the observed tissue characteristic value and the determined effect of the vessel pathology on the at least one tissue characteristic.

2. The computer-implemented method of claim 1, further comprising:
    using the observed tissue characteristic and the determined effect of vessel pathology on the at least on tissue characteristic to identify a patient vascular model that corresponds to the observed tissue characteristic value; and
    estimating, using one or more computer processors, the one or more patient pathological characteristics further based on the identified patient vascular model.

3. The computer-implemented method of claim 1, wherein the observed tissue characteristic value includes a perfusion value or a myocardial wall motion value.

4. The computer-implemented method of claim 3, further comprising:
    receiving the perfusion value or the myocardial wall motion value from one or more images of either the patient or one or more individuals of a plurality of individuals; and
    registering the perfusion value or the myocardial wall motion value to a tissue model of the patient.

5. The computer-implemented method of claim 1, further comprising:
    identifying a set of hypothetical vessel pathologies that produce the observed tissue characteristic value, wherein the one or more patient pathological characteristics are associated with the set of vessel pathologies.

6. The computer-implemented method of claim 5, further comprising:
    receiving a geometric model of the patient's anatomy; and applying computational fluid dynamics analysis to one or more deformed versions of the geometric model of the patient's anatomy, wherein the identification of the set of hypothetical vessel pathologies is based on the application of computational fluid dynamics analysis to the one or more deformed versions of the geometric model.

7. The computer-implemented method of claim 5, further comprising:
comparing a plurality of computational fluid dynamics analysis results associated with one or more models of the patient's anatomy with the observed tissue characteristic value; and
selecting a coronary model of the patient's anatomy based on the comparison of the plurality of computational fluid dynamics analysis results with the observed tissue characteristic value.

8. The computer-implemented method of claim 1, further comprising:
outputting a treatment associated with the one or more patient pathological characteristics.

9. A system for evaluating a patient with vascular disease, the system comprising:
a data storage device storing instructions for evaluating a patient with vascular disease; and
a processor configured to execute the instructions to perform a method including:
receiving a tissue model of the patient;
receiving a vascular model defining one or more vessel pathologies at a location of vasculature supplying blood to the tissue model;
modeling perfusion resulting from a first vessel pathology of the vascular model supplying blood to at least a portion of the tissue model;
computing, from the modeled perfusion resulting from the first vessel pathology, a first tissue characteristic value of the tissue model in response to the first vessel pathology, the tissue characteristic including a measure of tissue viability, a tissue capacity to change blood flow, a tissue irregularity, a tissue electrical property, and/or a tissue mechanical property;
modeling perfusion resulting from a second vessel pathology of the vascular model supplying blood to at least a portion of the tissue model;
computing, from the modeled perfusion resulting from the second vessel pathology, a second tissue characteristic value of the tissue model in response to the second vessel pathology;
determining an effect of vessel pathology on the at least one tissue characteristic, from a comparison of the first tissue characteristic to the second tissue characteristic;
receiving an observed tissue characteristic value associated with a patient; and
estimating, using one or more computer processors, one or more patient pathological characteristics at a location in the patient's anatomy using the observed tissue characteristic value and the determined effect of the vessel pathology on the at least one tissue characteristic.

10. The system of claim 9, wherein the system is further configured for:
using the observed tissue characteristic value and the determined effect of vessel pathology on the at least one tissue characteristic to identify a patient vascular model that corresponds to the observed tissue characteristic value; and
estimating, using one or more computer processors, the one or more patient pathological characteristics further based on the identified patient vascular model.

11. The system of claim 9, wherein the observed tissue characteristic value includes a perfusion value or a myocardial wall motion value.

12. The system of claim 11, wherein the system is further configured for:
receiving the perfusion value or the myocardial wall motion value from one or more images of either the patient or one or more individuals of a plurality of individuals; and
registering the perfusion value or the myocardial wall motion value to a tissue model of the patient.

13. The system of claim 9, further comprising:
identifying a set of hypothetical vessel pathologies that produce the observed tissue characteristic value, wherein the one or more patient pathological characteristics of the patient are associated with the set of vessel pathologies.

14. The system of claim 13, wherein the system is further configured for:
receiving a geometric model of the patient's anatomy; and
applying computational fluid dynamics analysis to one or more deformed versions of the geometric model of the patient's anatomy, wherein the identification of the set of hypothetical vessel pathologies is based on the application of computational fluid dynamics analysis to the one or more deformed versions of the geometric model.

15. The system of claim 13, wherein the system is further configured for:
comparing a plurality of computational fluid dynamics analysis results associated with one or more models of the patient's anatomy with the observed tissue characteristic value; and
selecting a coronary model of the patient's anatomy based on the comparison of the plurality of computational fluid dynamics analysis results with the observed tissue characteristic value.

16. The system of claim 9, further comprising:
outputting a treatment associated with the one or more patient pathological characteristics.

17. A non-transitory computer readable medium for use on a computer system containing computer-executable programming instructions for performing a method of evaluating a patient with vascular disease, the method comprising:
receiving a tissue model of the patient;
receiving a vascular model defining one or more vessel pathologies at a location of vasculature supplying blood to the tissue model;
modeling perfusion resulting from a first vessel pathology of the vascular model supplying blood to at least a portion of the tissue model;
computing, from the modeled perfusion resulting from the first vessel pathology, a first tissue characteristic value of the tissue model in response to the first vessel pathology, the tissue characteristic including a measure of tissue viability, a tissue capacity to change blood flow, a tissue irregularity, a tissue electrical property, and/or a tissue mechanical property;
modeling perfusion resulting from a second vessel pathology of the vascular model supplying blood to at least a portion of the tissue model;
modeling perfusion resulting from a second vessel pathology of the vascular model supplying blood to at least a portion of the tissue model;
computing, from the modeled perfusion resulting from the second vessel pathology, a second tissue characteristic value of the tissue model in response to the second vessel pathology;

determining an effect of vessel pathology on the at least one tissue characteristic, from a comparison of the first tissue characteristic to the second tissue characteristic;

receiving an observed tissue characteristic value associated with a patient; and estimating, using one or more computer processors, one or more patient pathological characteristics at a location in the patient's anatomy using the observed tissue characteristic value and the determined effect of the vessel pathology on the at least one tissue characteristic.

18. The non-transitory computer readable medium of claim 17, the method further comprising:

using the observed tissue characteristic value and the determined effect of vessel pathology on the at least one tissue characteristic to identify a patient vascular model that corresponds to the observed tissue characteristic value; and estimating, using one or more computer processors, the one or more patient pathological characteristics further based on the identified patient vascular model.

19. The non-transitory computer readable medium of claim 17, wherein the observed tissue characteristic value includes a perfusion value or a myocardial wall motion value.

20. The non-transitory computer readable medium of claim 19, the method further comprising:

receiving the perfusion value or the myocardial wall motion value from one or more images of either the patient or one or more individuals of a plurality of individuals; and registering the perfusion value or the myocardial wall motion value to a tissue model of the patient.

\* \* \* \* \*